United States Patent
Haber et al.

(10) Patent No.: US 6,366,802 B1
(45) Date of Patent: Apr. 2, 2002

(54) PHOTON IRRADIATION HUMAN PAIN TREATMENT MONITORED BY THERMAL IMAGING

(75) Inventors: Constance Haber, Murrysville, PA (US); Maurice Bales, Lafayette, CA (US)

(73) Assignee: Bales Scientific Inc., Walnut Creek, CA (US)

(*) Notice: Subject to any disclaimer, the term of this patent is extended or adjusted under 35 U.S.C. 154(b) by 0 days.

(21) Appl. No.: 09/482,465

(22) Filed: Jan. 13, 2000

Related U.S. Application Data

(63) Continuation-in-part of application No. 09/229,689, filed on Jan. 13, 1999, now Pat. No. 6,157,854.

(51) Int. Cl.$^7$ ................................................. A61B 5/01
(52) U.S. Cl. .................... 600/474; 600/549; 607/88; 607/102
(58) Field of Search ................................ 600/474, 549, 600/427; 607/88–90, 100, 102, 108–111

(56) References Cited

U.S. PATENT DOCUMENTS

| | | | | |
|---|---|---|---|---|
| 3,245,402 A | * | 4/1966 | Barnes | 600/474 |
| 3,798,366 A | * | 3/1974 | Hunt et al. | 600/474 |
| 4,901,730 A | * | 2/1990 | Vitori et al. | 600/474 |
| 4,972,244 A | | 11/1990 | Buffet et al. | |
| 5,001,608 A | * | 3/1991 | Kenrli et al. | 607/90 |
| 5,332,899 A | | 7/1994 | Wolny et al. | |
| 5,368,031 A | * | 11/1994 | Cline et al. | 607/100 |
| 5,413,587 A | * | 5/1995 | Hochstein | 607/100 |
| 5,503,150 A | * | 4/1996 | Evans | 607/102 |
| 5,507,790 A | * | 4/1996 | Weiss | 607/100 |
| 5,591,219 A | * | 1/1997 | Dungan | 607/100 |
| 5,849,026 A | * | 12/1998 | Zhou et al. | |
| 5,995,865 A | * | 11/1999 | Carioni | 600/474 |

FOREIGN PATENT DOCUMENTS

SU        1544-323       *  2/1990

* cited by examiner

*Primary Examiner*—Ruth S. Smith
(74) *Attorney, Agent, or Firm*—Tarolli, Sundheim, Covell, Tummino & Szabo L.L.P.

(57) ABSTRACT

Photo illumination of sites along a nerve supplying a painful region is conducted one at a time until a thermal image of that region or one related to it shows a significant change in temperature, at which time the treatment is terminated. If it is an extremity (hand or foot) that is has pain symptoms, one extremity is treated by exposing its nerve sites to photo illumination while the other extremity is observed by a thermograph instrument. Use of the thermal image as a feedback technique allows the treatment to be terminated as soon as the favorable temperature change takes place.

9 Claims, 2 Drawing Sheets

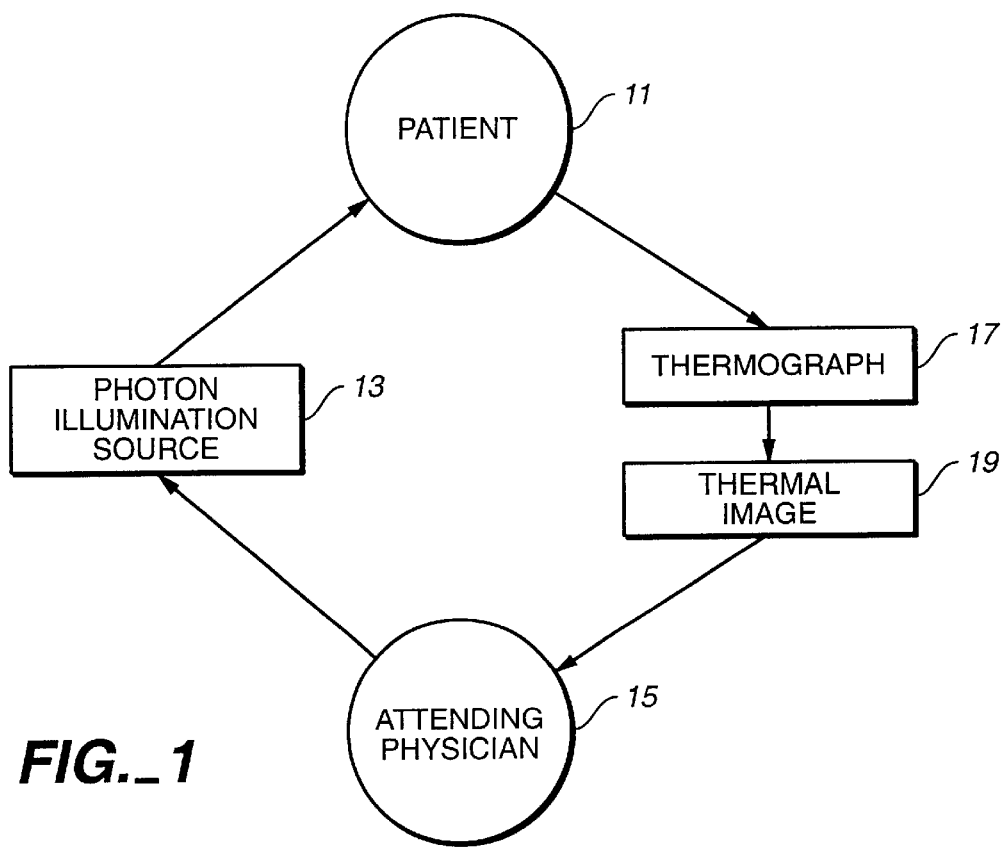
FIG._1
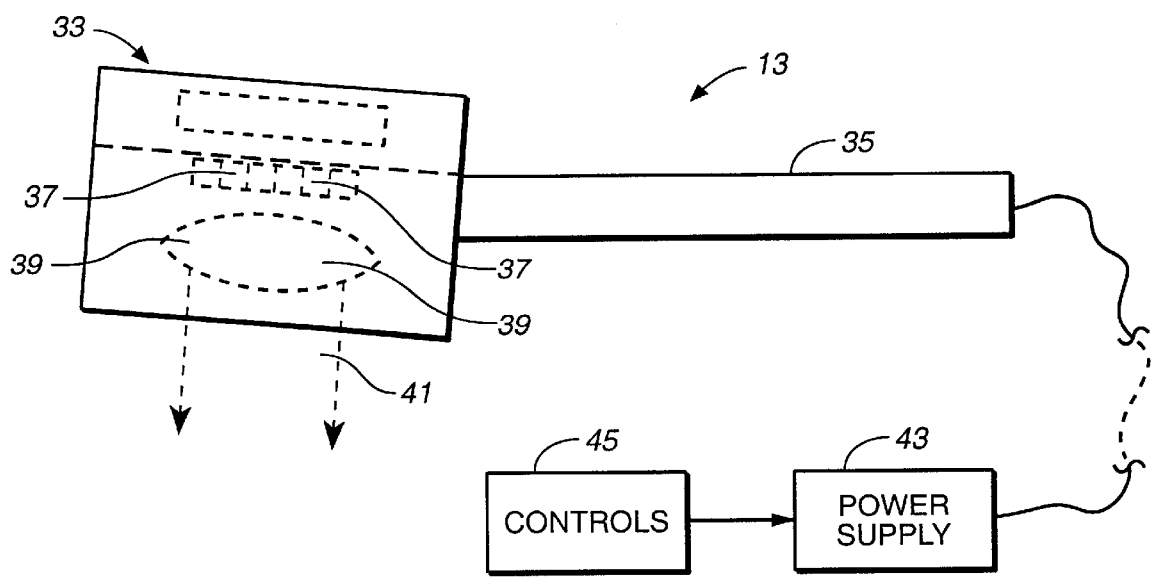
FIG._3

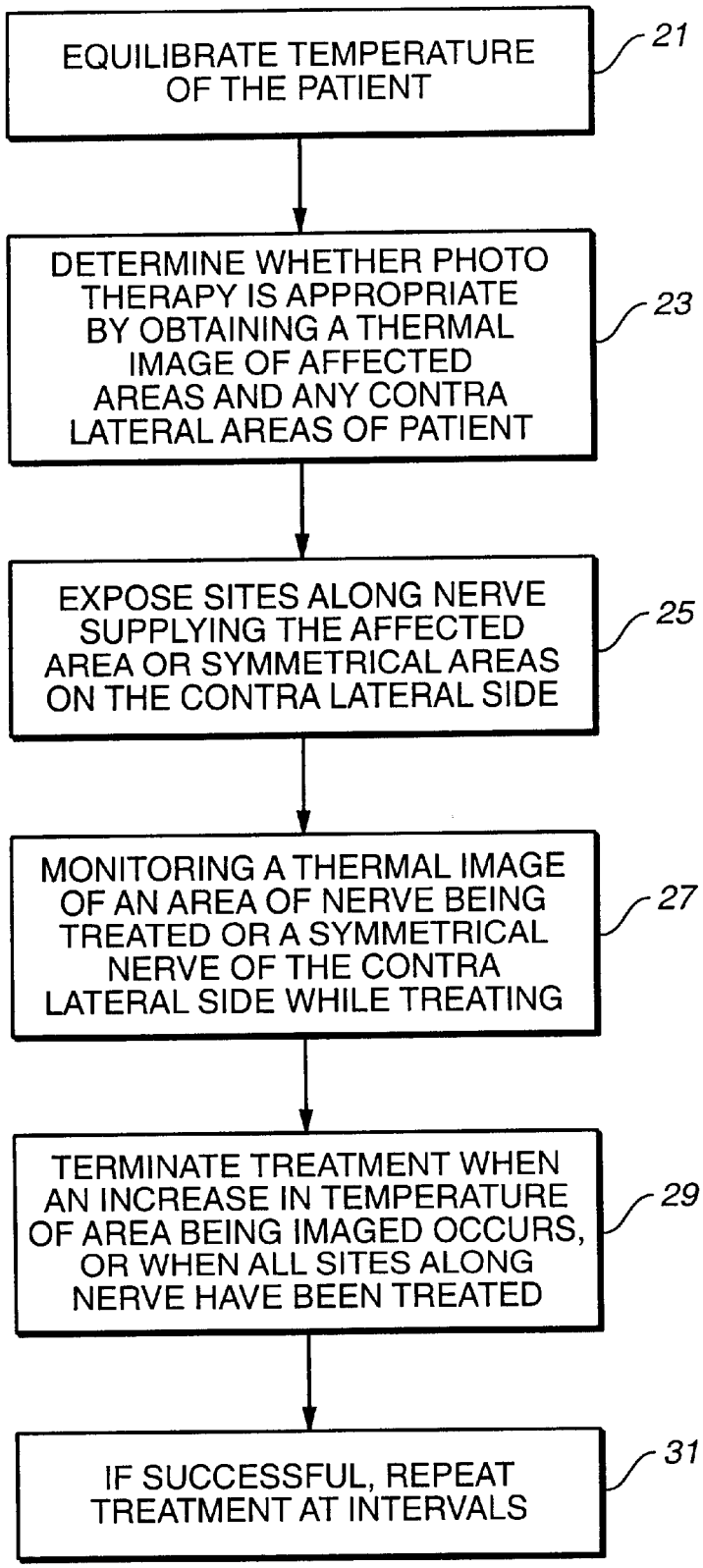
FIG._2

PHOTON IRRADIATION HUMAN PAIN TREATMENT MONITORED BY THERMAL IMAGING

CROSS-REFERENCED TO RELATED APPLICATION

This is a continuation-in-part of U.S. patent application Ser. No. 09/229,689, filed Jan. 13, 1999, now issued as U.S. Pat. No. 6,157,854.

BACKGROUND OF THE INVENTION

This invention relates generally to techniques of reducing or eliminating pain by application of infrared irradiation, and, more specifically, to methods and apparatus for monitoring the effects of such treatment as it is being conducted.

Infrared irradiation and low energy lasers are widely used as treatment devices for a number of medical conditions. Photons of energy are delivered to tissue below the surface of the skin without causing adverse effects of superficial heating of the skin. Raising the temperature of internal damaged tissue is thought to promote healing by increasing blood flow and stimulating the immune system. Nerves have also been treated by directing penetrating radiation through the skin at acupuncture sites in order to treat suspected causes of chronic pain. The primary technique for determining whether such treatment has been successful is to evaluate reports of the patient as to whether the pain has subsided.

It is an object of the present invention to provide improved techniques for evaluating and treating nerves with penetrating infrared irradiation in order to normalize their function thereby alleviating chronic pain.

It is another object of the present invention to provide improved techniques for determining the effect of the treatment.

SUMMARY OF THE INVENTION

These and other objects of the present invention are accomplished, briefly and generally, by treating nerves at known acupuncture sites with electromagnetic radiation, preferable non-coherent electromagnetic radiation in the infrared range of the spectrum. A large number of conditions that cause pain are able to be treated in this manner. Monitoring the treatment while it is occurring is accomplished by observing live thermal images of the temperature patterns of the afflicted area, which responds when the condition has been successfully treated by the photon stimulation.

Treatment sites along a nerve supplying the afflicted region of pain are treated one at a time, beginning with the site closest to the region and then proceeding away from the region along the identified nerve. As soon as the monitored thermal image changes in a manner to indicate the nerve has responded to stimulation, the procedure is terminated, continued treatment being unnecessary. This real time feedback to the attending physician of the effect of the treatment provides him or her with objectification of response to stimulation and eliminates unnecessary additional treatments. Without such feedback, the attending physician must complete applying infrared irradiation to all chosen sites along the specific nerve and then wait for a subjective report from the patient as to whether the pain has decreased or gone away. Although the unnecessary further treatments are not known to cause any harm, they would extend the duration and cost of the treatment. It is usually desirable to repeat the treatment several times, at intervals of at least several hours to several days. During such repeated treatments, the attending physician need expose only those sites determined by the thermal imaging of the first treatment to be sufficient.

One specific application of the present invention is in the treating of an extremity (hand or foot) in which the patient is experiencing pain, such as the continuous diffuse limb pain of complex regional pain syndrome (CRPS). In this case, the nerve sites of one of the painful extremities and the other contralateral extremity is treated and the corresponding region of the extremity not being treated is imaged by high-resolution telethermographic instrumentation. As soon as the attending physician notes that the temperature of the monitored extremity has changed, treatment of the other extremity may be terminated. No other sites along an identified nerve are treated after the temperature change takes place.

Additional objects, advantages and features of the various aspects of the present invention will become apparent from the following description of its preferred embodiments, which description should be taken in conjunction with the accompanying drawings.

BRIEF DESCRIPTION OF THE DRAWINGS

FIG. 1 conceptually illustrates a patient's treatment process with a thermal feedback image;

FIG. 2 is a flow diagram outlining the steps of carrying out treatment according to FIG. 1;

FIG. 3 illustrates the photon illumination source of FIG. 1.

DESCRIPTION OF THE PREFERRED EMBODIMENTS

The diagram of FIG. 1 very broadly illustrates the treatment procedures of the present invention. Selected sites of a patient 11 are treated with infrared irradiation from an illumination source. The radiation is within the infrared portion of the electromagnetic energy spectrum and is approximately one micron in wavelength. The wavelength is chosen to penetrate into tissue through the skin. Although a laser can be used as the illumination source, it is preferable to use a non-coherent infrared source having a small wavelength spread. Such a source is easier to control and use than a laser; this is less likely to be the inadvertent cause of any damage to the patient.

A thermograph 17 is positioned to receive a thermal image 19 of an appropriate area of the patient 11. The thermograph 17 may be used to constantly display that image in real time, on its video color monitor, or periodically provide a thermal image after each exposure, either on its monitor or in printed form, after each site exposure of the patient. In either case, lines of constant temperature are preferably superimposed on the patient image, and the image is shaded with different colors to show regions that are at the same temperature. Such a thermograph is available from Bales Scientific, Inc., of Walnut Creek, Calif. Although any infrared imaging device would allow the attending physician to determine when the temperature of the imaged patient area changes, a high-resolution telethermographic apparatus is preferred.

The treatment procedure is outlined generally in the flowchart of FIG. 2. A first step 21 is to place the patient in a room of a constant temperature, until the patient's temperature is stable. A next step 23 is to confirm that the procedure is likely to benefit the patient. In addition to hearing the patient's description of his or her pain symptoms, a thermal image is taken of at least the affected region of pain. Irregular isothermal contours in the image indicate a condition that can potentially be treated by the present invention. If the affected region is on a limb (arm or leg) or an extremity (hand or foot) a thermal image of the corresponding region on the contralateral limb or extremity also provides useful information. If the thermal images of the affected and contralateral regions show significantly different temperature distributions, this is further evidence of a condition that is treatable by photon illumination techniques of the present invention.

In a step 25, acupuncture sites along a nerve that supplies the affected region are treated with infrared irradiation by the source 13, one at a time, beginning with the site furthest into the affected region, or nearest to it, if there is no site identified to be within the affected region. If the physician chooses, the contralateral region could be treated initially to determine the patient's sensitivity.

Simultaneously with the treatment being performed, or at least after each site exposure, a thermal image is acquired and reviewed by the attending physician, as indicated by a step 27. Both treated and contralateral sites are evaluated and reviewed. Contralateral sites also exist throughout the body in regions other than in a limb or extremity. For example, a site of pain on the back a distance from the spine has a contralateral site the same distance on the other side of the spine. However, in cases where no contralateral region exists, the thermal image is taken along the same nerve being treated but a distance from the affected region. In either case, the thermal image can alternatively be taken of the region being exposed to the infrared irradiation after each site exposure but this is not preferred.

As soon as the attending physician observes a significant change in the temperature of the monitored region, treatment is terminated, as indicated by a step 29. This indicates successful treatment. If, on the other hand, no such temperature change is noted after all the sites along the identified nerve have been treated, it is concluded that the treatment is not being effective and no further such treatment is required.

But if the treatment is successful, it is usually desirable to repeat exposure of the same sites in each of one, two, or even more subsequent sessions, as indicated by a step 31. In an extreme case, these sessions may be had with only a few hours between them. In the more usual case, a treatment session is held every other day or so. The subsequent treatments are usually limited to treating the same sites as during the first treatment. Thermal imaging need not always be done in real time during the subsequent treatment sessions since it has already been determined, in the first session, the site exposure pattern that brings about positive results. But a thermal image is generally desirable to have at the end of each session in order for the attending physician to determine when a desired level of thermal equilibration has been reached in the affected region, or between the affected and contralateral regions.

By using thermal imaging in real time during at least the first treatment, the effectiveness and objectivity of the treatment are established. This is better feedback than can be provided by the patient alone, who may not experience a reduction of end of his or her pain symptoms for some time after the treatment. Even if there is an earlier change in the symptoms, the patient's report is subjective in nature and may not be accurate.

A preferred form of illumination 13 is shown in FIG. 3. A housing 33 is attached to an end of a handle 35. A two dimensional array of infrared emitters is carried within the housing 33. However, an illuminator having a diode mosaic array can also be advantageously used. The radiation emitters are non-laser emitters. The wavelengths included in the radiation emitted are distributed around 950 nanometers, in a specific example. An optical system 39 gathers diverging radiation from the emitters and forms and approximately collimated beam 41. For the applications described herein, the beam 41 is made to be about one inch in diameter. This is large enough to be able to treat each individual nerve site without having to be precisely aligned with and directly pointed to the site. The emitters 37 are electrically driven by a power supply 43 that includes controls 45. The controls 45 can be implemented in a manner to make it easy for the attending physician to set the duration and level of each radiating exposure. In some circumstances, it may also be desirable to modulate the intensity of the radiation during the exposure.

It is believed that the photon treatment functions by improving communication between sensory and sympathetic nerves that have become altered. Without proper communication, it is opined, the sympathetic nerves cause blood vessels to constrict and keep a region of the body from receiving an adequate flow of blood. The lack of adequate blood flow causes perpetuation of the chronic pain symptoms that results in the patient seeking treatment. It is believed that communication between the sensory and sympathetic nerves are reestablished as a result of the photon energy being absorbed by nerve cells that communicate between the two. Since the treatment technique is not invasive, it is very safe for the patient and operator.

Dramatic results have been obtained during treating complex regional pain syndrome (CRPS) in the hands or feet. The painful extremity and the contralateral one are initially thermally imaged. If the images show an average temperature difference between the extremities of 0.5° or more, the photon treatment will likely follow. The acupuncture sites of the warmest of the two extremities are treated one site at a time with infrared irradiation. The other extremity is viewed with the thermograph instrument. As soon as a significant change in the temperature of the other extremity is observed from the thermal image, the treatment is terminated. The same set of sites is treated about two days later and again about two days after that. The subsequent treatments are primarily designed to prevent regression.

Acupuncture

Photon therapy lends itself well to principals and practice of acupressure or acupuncture. The doctor uses the standard methods of examination, evaluation, and case planning. After the physician selects the points to be treated, photon therapy is applied to the designated area for 30 seconds for the first visit. On the following visit, if the desired result has not been obtained, the time may be increased proportionately. If the patient experiences the flow of chi or paresthesia, the treatment is suspended at that site. The physician then determines the need for additional treatment.

Many doctors have been successful using electroevaluation of the origin and termination of meridians on the fingers and toes. After the appropriate acupoints have been selected, located and marked, photon therapy is then applied. The doctor assesses the energy of the meridians and applies additional photon therapy to the desired points.

Other doctors have elected to use prescriptives or formula for treatment. The acupoints are selected and recorded in the chart. The physician then directs the intensity and duration of photon therapy for a given number of treatments. After the designated number of treatments, a comparative examination is conducted. The location, duration and intensity of photon therapy are adjusted accordingly.

Doctors have also been very successful in applying photon therapy to alarm points or by using Shakra points to augment the patient's energy level. These treatments however, are highly specialized and must fall within the physician's specialty, training and expertise. Photon therapy has been adaptable to the various physician specialty needs.

Articular Mobilization or Manipulation

If the physician chooses manipulation or mobilization of articulations that are demonstrating subluxation and restriction of segmental motion, the application of photon therapy is efficacious. A thirty-second treatment is applied to the articular facets of each spinal segment to be manipulated. The painting technique is then used along the paraspinal tissues and the manipulation is performed. The painting technique is again applied to the paraspinal area.

When manipulation of the large articulations of the body are to be performed, photon therapy is applied at 30 second increments through the joint at right angles. If any muscle tension signs are noted, the painting technique is administered, the joint manipulated, and the tender areas again painted.

If muscle spasm or pain is complicating the manipulative procedure, ask the patient to place the index finger on the specific point of pain. Apply one-minute photon therapy to the spot and again begin to perform passive range of motion. Continue to identify and apply photon therapy to the region of pain. Once a tolerable level has been reached, perform the necessary procedure and then apply photon therapy to the remaining sensitive area if present.

Utilization of photon therapy has been able to assist the physician in obtaining joint cavitation not dissimilar to manipulation under anesthesia and without the potential deleterious effects of prescriptive medications and within the economic confines of today's restrictive practices.

Multiple levels of manipulative procedures are able to be accomplished in a quick and concise fashion. Physicians have indicated that much less directive thrust is required following photon therapy administration and joint fixations am much more readily resolved.

If the patient is slight of build, elderly, or constitutionally weak, adjust the magnitude of therapy downward. A second or third application of therapy is preferred to overwhelming the patient's adaptive response.

Carpal and Tarsal Tunnel Syndromes

Begin photon therapy for a one-minute period at the site of compression. Select the most distal point of electrodiagnosis and again apply one minute of treatment. An additional more proximal point is then treated. Proceed to the area of isolated supply for the involved nerve and use a painting technique. The duration should be at least a minute or two and relevant to the surface area of involvement. Use slow circular patterns at the nail beds and then linear sweeping motion at the phalanges. Return to the area of suspect compression and provide additional treatment. In many instances, the patient will begin to experience a tingling, warm, or cold sensation in the involved nerve distribution. This is the signal to terminate photon therapy at that site.

If the physician is able to use thermal imaging as a live monitoring guide, the treatment is terminated as soon as bilateral symmetry or active change begins. If the affected region begins to degrade in emissivity, treatment at that site is terminated immediately.

Palpate the proximal muscle bellies searching for trigger points, muscle spasm, or taught nodular bands. These regions should be treated with a continuous application of photon therapy at the active trigger point, or with a painting technique along the belly of the involved musculature.

The average course of treatment for a non-surgical tunnel syndrome is approximately six sessions. Reoccurrence of the symptoms following surgery usually requires an extension in the duration of the total course of case care. If objectification of improvement is continued and additional functional gains documented, further continuance of treatment is appropriate. Treating the scar if present is recommended. Apply photon treatment to the involved nerve along its distribution. Be sure to use areas of pure innervation for the involved nerve, the points of electrostimulation in electrodiagnosis, or acupoints along the peripheral distribution.

Complex Regional Pin Syndrome

Treatment of this condition should not be undertaken without a high-resolution telethermographic evaluation with monitoring during the initial photon treatment session.

The photon stimulation directly affects the autonomic nervous system thereby creating a potential for over stimulation in this condition. CRPS requires much more planning and treatment consideration before photon treatment is applied. After viewing the thermal image the physician selects the electrodiagnostic point or acupoint of the affected nerve of the contralateral side. Treatment is applied to that site for no greater than 60 seconds. If the affected extremity begins to evidence a degradation in temperature, treatment at that site is discontinued and that point documented in the daily record. If however, there is an increase in emissivity, treatment may continue. In each of these cases considerable patient individuality is expressed. The physician continues to establish active points and exclude counterproductive ones. Consideration can be given to application of photon therapy to the nail beds, the spinal level, acupuncture points or characteristic sites used for nerve blocks. The physician should record the effective sites based on documented imaging evaluation and treat those points for two or three additional sessions until another imaging evaluation is performed.

After comparative objective evaluation is performed, the physician again amends the treatment plan based on the thermal evaluation. Certain regions will have responded more quickly and can be deleted from the treatment plan, recalcitrant regions however, must be treated differently. Changes in the plan could be treatment from proximal to distal instead of distal to proximal, treatment on the affected extremity instead of the contralateral side, treatment applied only to electrodiagnostic points et al.

The duration of the condition necessitates consideration. The longer the patient has been affected, the more cautiously the treatment should be applied.

If multiple extremities are involved, concentrate on one only until it begins to respond then add gentle treatment to the other involved regions. Avoid over stimulation. If the physician deems that the severity of the condition demands aggressive measures, daily treatment can be provided for up to four days. The patient then should be rested for a day before treatment begins again.

When the hyperpathia begins to decrease, the patient is encouraged to gently move the extremity during the application of photon therapy. Even if only the fingers or toes can be slightly moved, additional treatment benefits can be obtained. The patient must be encouraged to continue movement of the involved extremity has much as can be tolerated.

In the majority of cases, treatment is cumulative. Each treatment is beneficially added to the previous one. The full benefit of the treatment administered today cannot be appreciated for eight to ten hours. Many times a patient will not indicate a subjective response, but the thermal imaging demonstrates a decided change toward thermal symmetry. When they return for care the next day, there has been sustained improvement in thermal emissivity. This is an objectification of an effective treatment. If, however, several treatments have been disbursed and no improvement is noted either subjectively or objectively, treatment should be discontinued.

Establishing function of the autonomic system is not accomplished hurriedly, especially if invasive methods including nerve blocks, bier blocks, stimulators or chronicity of condition is in evidence. A slow and continuous improvement in function and decrease in pain levels is expected.

The high-resolution thermal imaging examination is the "gold standard" for the autonomic system. Evidence of improvement supports continuation of care. If, however, a further decrease in emissivity is evidenced, treatment must be terminated.

Geriatric Considerations
Phalangeal Joint Contracture

Many mature persons suffer from spontaneous phalangeal joint contractures of non-traumatic origin. In most instances, the symptomatic complex varies from pain to insensitive toes. The toes are more frequently involved, but contracture may occur in the fingers.

Involvement in the pedal foundation is usually bilateral and joint deformity with overlapping toes may occur. The patient usually has difficulty voluntarily separating the toes or performing flexion or extension. The gait may be altered due to toe inflexibility. Application of one minute photon therapy at intensity 7 is applied at the deep fibular (peroneal), sural nerve via lateral dorsal cutaneous branch and posterior tibia nerves. Then the toes should be painted on both the dorsal and plantar aspects for one minute each. Following this treatment thermal imaging will reveal a marked hypothermia when compared to the initial evaluation. At this time, gentle mobilization of all toes is performed. The patient should then be instructed in mobilization exercises.

The fingers are much more accessible and the involvement is usually specific in lieu of extensive. Treatment commences by photonic stimulation of 1 minute duration at intensity 7 at the flexor retinaculum for the median and ulnar nerves. The involved fingers are then treated with a slow painting beginning proximal and continuing distal on both the dorsal and palmar surfaces. If palpatory examination reveals specific tendinous thickening or contracture, a one-minute period of continuous application should be made. Thermal imaging evaluation will document hypothermia of the affected tissues as the desired outcome. At this time, mobilization of the affected articulations should occur. Many seniors are unable to tolerate prolonged hypothermia of the extremities and application of an additional modality is appropriate. Success has been obtained with slow warming therapies such as paraffin baths, low intensity microwave or diathermy, or application of hot fomentation's for 15 minutes.

Most seniors respond within 1 or 2 photonic treatments with a demonstration of increased range of motion and improved sensibility. Treatment duration is usually 4 sessions and then on a PRN basis.

Articular Dysfunction

Many articular joint dysfunctions occur because of deduced movement coupled with degenerative changes. Photonic stimulation should be applied at right angles to the joint at one-minute periods. Then, passively move the joint through the range of motion. When restriction or pain is noted, use the photonic stimulator in a painting fashion parallel to the muscle fibers and then point specific to the painful site.

Proceed to restore full passive range of motion to the most optimal degree. Have the patient then perform active range of motion and provide photonic stimulation to any area of joint restriction or pain.

Age is not a barrier to benefit from photonic stimulation. This treatment, due to the absence of adverse side effects in the presence of overmedicated patients, provides efficient and effective pain relief with a concomitant improvement in joint function.

Headache

Headaches from a wide variety of etiologies can be effectively treated.

Tension Headache

Tension headaches respond well by painting the trapezli with photon therapy. Begin at the suboccipital area and continue in slow smooth parallel motions to terminate at the acromioclavicular articulation, scapula or the mid-thoracic spine. The frontalis and temporalis muscles are treated in a similar fashion following the origin and insertion of the muscle. The patient should keep their eyes closed and wear protective eyewear when any facial region is treated. The suboccipital musculature is treated with a one-minute static treatment applied at the site one third between the mastoid and the spine. This site correlates with the acupoint GB20. The final site to be treated is immediately beneath the ear in the triangle groove formed by the skull and the mandible. It is recommended that treatment is provided bilaterally but if the headache is unilateral, then only the affected side is treated.

Sinus Headache

Provide the patient with protective eye wear. Apply photon treatment immediately over the frontal sinus with a painting technique for one minute. Locate the acupoint Bladder 2. In a supine position, the point is located at the medial end of the eyebrow, in the supraorbital fissure. Use one-minute treatment at this site. The next point to be treated is LI20, which is located on the superior part of the nasolabial groove. Again, apply one-minute photon treatment. The final point is located at the inferior fossa of the nasal bone, at the superior end of the nasolabial groove at the intersection of the nose and the face. The concluding treatment is provided with a painting technique along the cervical lymph chain for one minute bilaterally.

Vertebrogenic Headache

Determine the vertebral level of involvement with standard diagnostic methods. Apply the photon therapy on the lateral aspect of the neck corresponding to the involved area. The treatment is administered bilaterally for one minute on each side. If the patient's neck is particularly small or large, adjust the time appropriately. Manually mobilize the involved segment, or if appropriate, perform a manipulation. Apply the photon therapy to the remaining tender soft tissues. Search the area manually for trigger points or taut musculature that could impede the range of motion. Distal points proven effective include the point one inch above the fossa of the olecranon process of the ulna. The treatment is concluded with passive range of motion of the cervical spine.

Intervertebral Disc Syndrome

Begin photon therapy immediately over the involved disc. Apply one minute of therapy and then move to the second site that would be approximately one-inch lateral. Again apply one minute of continuous photon treatment. If the involved nerve has a cutaneous isolated supply, apply a one-minute treatment in a circular fashion bilaterally. Next, proceed to the electrodiagnostic point for the involved nerve and apply a one-minute application at that site without moving the applicator. If radiculopathy is present, adding a second or even a third point on that nerve is advantageous.

The physician may elect to administer photon treatment to acupoints along the involved nerve or at points of control located at remote sites.

Palpate along the involved nerve for areas of hypersensitivity or trigger points located within the muscles innervated by the nerve. High-resolution telethermography is necessary in establishing the effective points. Usually, the peripheral distribution is hypothermic when compared to the contralateral side. The immediate goal of the treatment is to increase the peripheral perfusion of the involved extremity. Many times this can be accomplished by treating the contralateral spinal level then the electrodiagnostic point. If there is a further degradation in emissivity, discontinue treatment at that site and return to the ipsilateral points.

Photon therapy applied daily for four days should be sufficient to establish sustained improvement subjectively and objectively with a normalization of the thermal imaging. Immediate referral and discontinuance of therapy should occur if there has been no progress.

Photon therapy has been effective in pain control prior to surgery. The patients receiving therapy have needed less medication, maintained an increased activity level and have been able to sleep longer periods before awakening.

Patients suffering bulged or protruded discs are treated similarly. The progress is more rapid and discharge should occur in approximately 6 to 10 treatments. If the disc problem is in the cervical region, be sure to treat the lateral aspect of the involved segment bilaterally. Slow gentle range of motion of the cervical spine has been efficacious during the application of photon therapy.

Some physicians have elected to incorporate photon therapy combined with traction (flexion distraction, long axis, et al), especially if the patient complained of stiffness or soreness following the mechanical procedure.

Paint the symptomatic region with a parallel sweeping motion for a minute, and then apply one-minute continuous treatment to each involved disc. Perform the mechanical procedure and again repeat the painting technique. Please note that if traction has already been used and photon treatment is being added, the intensity of traction should be reduced. The photon therapy apparently permits a deeper tissue relaxation; ergo less force should be used.

Muscle Injury with Ecchymosis or Swelling

Begin treatment by locating the major lymph concentration proximal to the injured tissue and closest to the trunk; apply one minute of photon therapy. Select the next lymph aggregate if the injured tissue is more distal on the extremity and treat the region for one minute. Now proceed to the region of swelling. Use the painting technique beginning distally and moving proximally. One or two minutes should be sufficient if the swelling does not extend beyond the second joint margin. Using light digital palpation, select tender and sensitive muscle fibrils and treat for 15 to 30 seconds. If the patient indicates any area of hypersensitivity or paresthesia, immediately discontinue treatment at that area.

In cases of hypersensitivity to light digital palpation or acute injury, the pulse mode has been able to be more readily tolerated. The lower pulses are selected for slow, deep penetration. They seem to permit the tissues to respond without over-reaction. The painting technique or slow circular movements over the ecchymosis or swelling is mandated to ensure fluid movement and avoidance of hypersensitivity in acute stages. With the passage of time, the continuous mode is able to be employed.

Adding one-minute of photon therapy to the nerve root of the innervated tissue has been beneficial.

Myofascial Pain Syndrome

Successful treatment of this condition with photon therapy necessitates: 1. The physician makes an appropriate diagnosis based upon history and physical examination, 2. The specific muscle(s) are identified with respect to mechanism of injury, 3. TPs are identified with zone of radiation produced upon compression, and, 4. Documentation consisting of pain drawings, algorimetry, or telethermography is kept.

Treatment consists of applying photon therapy directly to the TP for 1 minute. The origin and insertion of the muscle is then treated in a similar fashion if possible. A painting technique (slow smooth even strokes) paralleling the muscle fibers is then performed. The duration of this technique is based upon the muscle length or approximately one to two minutes. Each muscle identified by the doctor to be treated is begun with the most painful treated first. No additional treatment is performed that session.

The next session is begun with an assessment and updating of the daily record. Any of the painful areas that have been resolved are not treated. The remaining tender regions are treated as in session one. When the painting technique is to begin, the patient is asked to move the injured, part in a slow smooth pain free range of motion and the treatment continues until all areas are treated.

The third session again requires evaluation, elimination of resolved areas, and treatment of the TP, origin and insertion of the involved muscle. The physician then uses the painting technique with a gentle stretch applied to the affected muscle. As the physician notes an improvement in the elasticity of the muscle and a concomitant improvement in range of motion and reduction of pain, additional tension can be applied.

One treatment session would usually not exceed three specific muscles in any one given region. In an acute case, treatment could be administered daily not to exceed three or four days. Provide a rest day between treatments as soon as symptom reduction and palpable decrease in the TPs can be noted. Avoid over treating. An uncomplicated case should be resolved within six visits.

High-resolution telethermography is able to document each patient's response to photon therapy. The physician is then able to be very specific with the duration of photon therapy and document sustained improvement with subsequent examinations.

Myositis & Myospasm

Place the part to be treated in a non-dependent or weight bearing position. Have the patient seated in a comfortable chair or massage chair for the cervical spine, or in a side lying posture for the lumbar spine. Use the painting technique beginning at the distal portion of the muscle and parallel the fibers to the proximal portion. Use a gentle stretch while painting and after the third or fourth pass, begin voluntary contraction with resistance applied by the doctor. The total treatment of one muscle would be from 3 to 5 minutes depending on the length of the muscle. An uncomplicated case should resolve within three or four sessions.

If the spasm is acute, such as in an automobile accident or athletic event, be sure to evaluate the muscle antagonist. If the patient is able to specifically localize a tender spot evidenced with contraction, apply continuous photon therapy to that specific site for one-minute then again retest.

In many instances, applying one minute of therapy to the ipsilateral nerve root of the involved muscle has hastened the tissue response to therapy.

Orificial Conditions

Gingivitis

In addition to the standard medical treatment, photon therapy may be used as an adjunctive treatment. With gloved finger, retract the buccal mucosa to permit photon therapy to be applied in a painting fashion along the gingival plane. Use maximum lamp and equipment intensity. Move the beam in a slow linear fashion beginning at the posterior portion of the molars and terminate at the central incisors. This exposure should be one minute and then the opposite side treated. Both the interior and buccal planes of the teeth should be treated.

Dental Extraction Pain

With gloved finger, gently retract buccal mucosa. Use maximum intensity lamp and output and apply photon therapy at the extraction site while slowly painting the region. Be sure to include remote regions of pain. Total oral exposure of photonic stimulation should not exceed 4 minutes.

Peripheral Neuropathy

The physician identifies the involved nerve(s) by standard diagnostic methods. The initial photon treatment begins at the spinal level and therapy is administered for one minute at the vertebral level(s) of the involved nerve. The site chosen is immediately lateral to the spinous process. The next site of treatment chosen is the most distal portion of the nerve at the most superficial site. The doctor may choose between the site of electrodiagnostic testing for the nerve or the acupuncture points located on the nerve. One-minute treatment is provided. The physician then palpates the muscles innervated by the nerve to determine if any abnormality exists. If nodular regions, taut bands, regions of hypersensitivity or TPs are identified, they too are treated. The path of the nerve, beginning distally and continuing proximal, may be treated with a painting technique.

It is expected that a subjective reduction of pain would occur within two treatments. If the patient is taking prescriptive medications, the prescribing physician would appropriately reduce them. In many instances, the patients have reported an ability to sleep longer. The pain has been reported to slowly diminish in intensity and character. If photon therapy has been applied to a very active point and a paresthesia is experienced, discontinue treatment at that location. If there has been surgery, be sure to provide additional treatment at the surgical site.

Polyneuropathy

Begin with treatment applied to the spinal nerves innervating the extremity(ies) involved using 30 seconds at each spinal level on the side of involvement. The next site selected is the center of the palm of the hand or plantar aspect of the foot. The superficial points of stimulation used in electrodiagnosis are treated for a one-minute period at each site. Use only three or a maximum of four sites per nerve. Always begin treatment gently using two or three sites. Allow the body sufficient time to respond to the stimulus before increasing duration or surface area of treatment. If the patient experiences paresthesias, immediately discontinue treatment at that site. If the physician determines the affected extremity outside the bounds of direct treatment (infection, plaster cast, etc.) the contralateral side should be treated until the restriction for treatment is lifted.

High-resolution telethermographic imaging is required to control dosages and determine treatment sites. The desired goal is to obtain bilateral symmetry of thermal emissivity. In some instances, the painful region is hyperthermic and in others hypothermic. Establishing symmetry has proven effective to reduce pain and empower function.

If the patient suffers from diabetic neuropathy, continuous monitoring must be performed. In many instances, insulin requirements decrease and appropriate physician prescriptives and prescriptive changes must be made. Treatment should not be undertaken unless appropriate medication changes can be met.

Non-allopathic providers must work in harmony with the attending physician or forgo treatment of this condition.

Post Surgical Pain

Begin treatment by using the painting method directly over the scar. Use slow circular motions for one minute. If the scar is exceptionally long, double the time. Now go to the spinal level of innervation for the surgical site and use a continuous one-minute treatment for each nerve level involved. Apply photon therapy bilaterally one inch lateral to the spinous process. If the surgical site is the spine, apply the therapy two spinal levels above and one level below the scar for a one-minute period at each site.

Return to the surgical site and, if sufficiently healed, gently palpate the scar and the surrounding tissues to locate any trigger points, areas of hypersensitivity, or taut nodular bands. Apply from 30 seconds to one minute depending on the sensitivity.

The surgical site is then treated with continuous photon therapy for a one-minute period. Move the applicator very slowly or not at all. The goal is to create a very slight erythema within the scar. If the patient feels a paresthesia, immediately terminate the treatment at that site.

If a zone of radiating pain is part of the symptom complex, identify the involved nerve or muscle. If the radiating pain is of neurogenic origin, apply one-minute photon treatment to the site of electrodiagnostic stimulation for the involved nerve. Begin with the most distal site and then continue proximally.

If the zone of radiating pain is of muscular origin, locate the active trigger point and apply digital compression of sufficient intensity to replicate the pain path. If the trigger point is very deep within the tissue or if it is exquisitely tender, use one minute of pulsed photon therapy followed by one minute of continuous. Re-examine the trigger point. It should feel more like a sponge and decidedly less tender to compression. Continue to search the muscle belly for secondary trigger points and record them in the chart. Do not treat them on the first visit unless the trigger point produces a radiating pain. These secondary points will in many instances disappear without further intervention. If they are still present on subsequent visits, they then could be addressed.

Another area of effectiveness is the zone of isolated supply. Use the applicator in a circular fashion within this region for a one-minute period. Treat this region bilaterally.

If the surgical site is sutured, photon therapy may be applied through liquid bandage or other clear dressings. DO NOT permit the applicator to come in contact with the patient or dressing and keep a smooth and slow applicator motion. Decrease the treatment time to thirty seconds. A second application could be provided at that area five to ten minutes later. If the patient experiences a paresthesia or a temperature alteration, immediately discontinue treatment.

Post Traumatic Sensory Nerve Dysfunction

This syndrome may also be produced by surgical transection, dental surgery, or other procedures. High-resolution telethermographic imaging will clearly reveal the involved segment with a specific hypothermia.

Apply photon therapy at intensity 9 in a circular pattern along the hypothermic cutaneous region. If appropriate, treat the spinal level bilaterally for one minute each. Return to the affected area and again treat for a one-minute period. Frequency is daily for 4 days, a day of rest, and if progress is objectified, a second series of 4 treatments administered on alternated days.

Rotator Cuff Injury

High-resolution thermal imaging will clearly reveal trigger points, myofascial involvements, or spasms affecting the rotator cuff. It will not reveal a tear. When performing the initial evaluation thermographically, carefully evaluate the distributions of the supra and infra spinatus, teres minor, and subscapularis. Apply one-minute photon treatments to each aberrant thermal finding. Then, passively range the shoulder. Each time the patient indicates a pain productive site, have them specifically localize it and again apply one minute of photonic stimulation. After all pain productive sites have been identified and treated, again perform a thermal image analysis. The anticipated goal is hypothermia of the affected area. If the patient is a senior citizen, apply a gentle, slow modality to increase peripheral perfusion. Otherwise, conclude the treatment. Following 4 to 5 photonic treatment sessions, begin a rehabilitative exercise program and provide photonic treatment at reduced frequency.

Shingles

Apply photon therapy for a one-minute period at the ipsilateral side of the vertebra at the level of the nerve roots of the involved tissue. The second treated site is the most distal portion of the nerve involved. Apply an additional minute of treatment. As soon as all the nerves are treated select the most proximal skin lesion. Do not permit the applicator to touch the lesion but move the applicator in a circular fashion around the perimeter of the lesion. Average approximately one minute of treatment for every centimeter of eruption. After the perimeter of each lesion is treated, use a painting technique to follow the path of the involved nerve and use parallel strokes moving from proximal to distal. If the condition is fulminating, daily treatment may be applied for four days then allow a one-day rest between the next series. Pain reduction should occur within the first two or three sessions and a noticeable change in the appearance of the skin within five.

Photon therapy may be successfully applied through prescriptive ointment and used in harmony with homeopathic, allopathic or nutrient therapeutics. If the patient experiences a sensation of warmth or paresthesia, immediately discontinue treatment at that site and proceed to the next.

If the face is being treated, be sure to provide the patient with protective eyewear.

Spondylosis

Identify through standard diagnostic methods each involved spinal nerve. Apply one minute of photon therapy immediately lateral to the spinous process of the relevant vertebra. Be sure to include two levels above and one level below the region of involvement.

Select the most distal point of electrodiagnosis and apply a one-minute treatment. Select additional superficial sites of that nerve and apply an additional one-minute treatment time.

Conclude the treatment with a painting technique parallel to the spinous processes. Proceed from cephalad to caudalward and treat the region from the spinous to the transverse process.

If necessary, additional acupoints may be added based on the overall treatment goals and considerations.

Sports Injury

After standard diagnostic methods have been employed and fracture and dislocation have been ruled out, photon therapy is appropriate to
1. decrease capillary bleeding
2. decrease swelling
3. decrease protective muscle spasms and
4. decrease pain.

High-resolution thermal imaging will clearly reveal specific regions of injury. Apply photon therapy at right angles to the involved joint at intensity 8 for 30 seconds each at the 4 joint planes. Use one-minute application at the origin and insertion of involved muscles and then paint the affected region for one minute on each surface of involvement. Thermal monitoring will control total dosage and a successful therapy will be reflected by hypothermia of the treated regions. Instruct the patient to use cool or ice packs for 10 minutes on and 20 minutes off for the next several hours. DO NOT warm the joint (tissue) with massage, hot packs, or other thermal methods to dissipate the joint hypothermia. After 72 hours, warming of the tissue is appropriate.

NEVER permit an athlete to "work out" or stress a joint or muscle following photon therapy due to the deep joint relaxation. At least 8 hours of recovery time must be permitted post treatment.

Temporomandibular Dysfunction

Thermal imaging is again exceptionally beneficial in evaluating this complicated region. Myofascial trigger points, sympathetic dysfunction and results of stress testing aid the physician in creation of the treatment plan. Stress testing is performed following thermal images of both side of the face with the jaw closed, then maximally open. The patient then performs five minutes of chewing. More stress is added if the patient is permitted to chew gum or pieces of fruit. Comparative thermal imaging is then repeated and the evaluations compared. Palpatory evaluation is performed with the jaw open, closed, and in the forward position. All areas of tenderness are marked on the patient with a skin pencil and recorded in the chart. Use a different color for each jaw position. There will be some points that are tender in the jaw forward position that are not in evidence on the other examinations Treat these areas first with 30 seconds of photon therapy. Now proceed to the points that are evident on the jaw open examination that are not on the others. Treat them with 30 seconds. Now finally, treat the points that are evident in the neutral examination that are not present on the others.

The final treatment is provided with a painting technique to the regions of tenderness that are present in the majority of the examinations. While the physician is applying the painting treatment, the patient opens and closes their jaw slowly.

If the contralateral TMJ is not pain productive with palpation it should not be treated. Examine the surrounding musculature of the scalp, suboccipital and upper cervical spinal segments to determine the presence of trigger points or segmental dysfunction. If found, these regions should be appropriately treated.

Torticollis

Palpate the affected sternocleidomastoid muscle to determine if a dense fibrous mass is able to be located within the muscle belly. If so, apply a one-minute application and repeat the examination. Continue to apply one minute series until a palpable difference in the consistency of the mass can be felt.

Use a painting technique beginning cephalad and continuing distal using parallel sweeping motion. Again evaluate the muscle tonus and reapply the one-minute series until palpable difference is felt.

Examine the ipsilateral spinal region C1 to C3. If there is tenderness to palpation repeat the painting technique. If specific foci of tenderness are palpated, use a constant one-minute application at that site. Motion palpate the segment to determine the need for manipulative therapeutics.

Examine the contralateral musculature and cervical vertebra. If muscle spasticity or hypomobility is found, again repeat the painting technique. Conclude the treatment with gentle long axis manual traction applied in the supine position. Be sure to keep the head in the midline and apply photon therapy on the side of deviation from the midline, should it occur.

This condition responds readily to care and the more rapidly treatment can be administered after onset, the more rapid the resolution of the symptomatic complex.

Although the various aspects of the present invention have been illustrated with respect to its preferred embodiments, it will be understood that the invention is entitled to protection within the scope of the appended claims.

It is claimed:

1. An apparatus for treating a human patient for pain, said apparatus comprising:
   a hand-held infrared illuminator for positioning over a selected site of the patient's body and for illuminating the selected site with infrared radiation having wavelengths of around 950 nanometers, said infrared radiation at around 950 nanometers penetrating a distance into the patient's body without damaging the patient's skin and sufficient to be absorbed by a primary nerve therein to cause regeneration of dysfunctional nerves and increase blood flow to thereby reduce pain in an area of the patient's body that is affected by the primary nerve, said illuminator having controls for setting a duration and level of radiation;
   a thermograph for providing thermal images of an area of the patient's body that include the primary nerve that is being illuminated or a corresponding nerve on a contralateral side of the patient's body, the thermal images changing in response to increased blood flow through the primary nerve;
   means detecting the changes in the thermal images; and
   means for terminating the illumination upon detection of the changes in the thermal images.

2. The apparatus of claim 1 wherein said illuminator includes a two-dimensional array of individual infrared radiation emitters and an optical system that images radiation emissions of said array into an approximately collimated beam.

3. The apparatus of claim 2 wherein said collimated beam is about one inch in diameter.

4. The apparatus of claim 2 wherein said infrared radiation emitters are non-laser emitters.

5. The apparatus of claim 1 wherein said illuminator includes a diode mosaic array.

6. An apparatus for treating a human patient for pain, said apparatus comprising:
   a hand-held infrared illuminator for positioning over a selected site of the patient's body and for illuminating the selected site with infrared radiation that penetrates a distance into the patient's body without damaging the patient's skin and sufficient to be absorbed by a primary nerve therein to cause regeneration of dysfunctional nerves and increase blood flow to thereby reduce pain in an area of the patient's body that is affected by the primary nerve, said illuminator having controls for setting a duration and level of radiation, said illuminator including a two-dimensional array of individual emitters of infrared radiation and an optical system that images radiation emissions of said array into an approximately collimated beam;
   a thermograph for providing thermal images of a surface of the patient's body that include the primary nerve that is being illuminated or a corresponding nerve on a contralateral side of the patient's body, the thermal images changing in response to increased blood flow through the primary nerve;
   means detecting the changes in the thermal images; and
   means for terminating the illumination upon detection of the changes in the thermal images.

7. The apparatus of claim 6 wherein said collimated beam is about one inch in diameter.

8. An apparatus for treating a human patient for pain, said apparatus comprising:
   a hand-held infrared illuminator for positioning over a selected site of the patient's body and for illuminating the selected site with infrared radiation that penetrates a distance into the patient's body without damaging the patient's skin and sufficient to be absorbed by a primary nerve therein to cause regeneration of dysfunctional nerves and increase blood flow to thereby reduce pain in an area of the patient's body that is affected by the primary nerve, said illuminator having controls for setting a duration and level of radiation, said illuminator including a diode mosaic array;
   a thermograph for providing thermal images of a surface of the patient's body that include the primary nerve that is being illuminated or a corresponding nerve on a contralateral side of the patient's body, the thermal images changing in response to increased blood flow through the primary nerve;
   means detecting the changes in the thermal images; and
   means for terminating the illumination upon detection of the changes in the thermal images.

9. An apparatus for treating a human patient for pain, said apparatus comprising:
   a hand-held infrared illuminator for positioning over a selected site of the patient's body and for illuminating the selected site with infrared radiation having wavelengths of around 950 nanometers, said infrared radiation at around 950 nanometers for penetrating a distance into the patient's body without damaging the patient's skin and sufficient to be absorbed by a primary nerve therein to cause regeneration of dysfunctional nerves and increase blood flow to thereby reduce pain in an area of the patient's body that is affected by the primary nerve, said illuminator having controls for setting a duration and level of radiation;
   a thermograph for providing thermal images of a surface of the patient's body that include the primary nerve that is being illuminated or a corresponding nerve on a contralateral side of the patient's body, the thermal images changing in response to increased blood flow through the primary nerve;
   means detecting the changes in the thermal images; and
   means for terminating the illumination upon detection of the changes in the thermal images;
   wherein said illuminator includes a two-dimensional array of individual non-laser emitters of infrared radiation and an optical system that images radiation emissions of said array into an approximately collimated beam having a diameter of about one inch.

\* \* \* \* \*